United States Patent
Neumann et al.

[11] Patent Number: 4,894,483
[45] Date of Patent: Jan. 16, 1990

[54] PREPARATION OF VINYLGLYOXAL DERIVATIVES, NOVEL VINYLGLYOXAL DERIVATIVES AND THEIR USE

[75] Inventors: Peter Neumann, Wiesloch; Hans-Dieter Martin, Duesseldorf; Roland Kramme, Hilden; Ralf T. Weimann, Duesseldorf, all of Fed. Rep. of Germany

[73] Assignee: BASF Aktiengesellschaft, Ludwigshafen, Fed. Rep. of Germany

[21] Appl. No.: 114,121

[22] Filed: Oct. 28, 1987

[30] Foreign Application Priority Data

Nov. 11, 1986 [DE] Fed. Rep. of Germany ....... 3638489

[51] Int. Cl.[4] .......................................... C07C 49/217
[52] U.S. Cl. .................................. 568/335; 568/412; 568/375; 568/376; 568/379; 568/381; 568/303; 568/337; 558/415
[58] Field of Search ............... 568/335, 412, 375, 376, 568/379, 381, 303, 337; 558/415

[56] References Cited

U.S. PATENT DOCUMENTS

| | | | |
|---|---|---|---|
| T887,006 | 6/1971 | Burness et al. | 568/335 |
| 2,698,820 | 1/1955 | Newcomer | 568/412 |
| 3,004,932 | 6/1961 | Dezsic et al. | 568/412 |

FOREIGN PATENT DOCUMENTS 1350741 of 1963 France ................................ 568/335

OTHER PUBLICATIONS

Kramme et al., Chem. Abst., vol. 106, #32324g (1987).
Tishchenko et al., Chem. Abst., vol. 71, #21941p (1969).
Russell et al., J.A.C.S., vol. 97, pp. 1900–1905 (1975).
Shepson et al., Chem. Abst., vol. 101, #96792n (1984).
Angew. Chemical, vol. 98, 1134–1136 (1986).
Synthesis, 309–310 (1980).
C.R. Acad. Sc. Paris, t272, Serie C, 233–235 (1971), Thuan et al.
J. Phys. Chem. 1984, 88, 4122–4126, Shepon et al.

Primary Examiner—James H. Reamer
Attorney, Agent, or Firm—John H. Shurtleff

[57] ABSTRACT

Vinylglyoxal derivatives of the general formula I

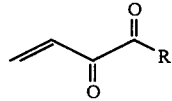
(I)

where R is straight-chain or branched alkyl or alkenyl, cycloalkyl or unsubstituted or substituted phenyl, are prepared by a process in which bicyclo[2.2.1]hept-5-enecarbaldehyde of the formula V

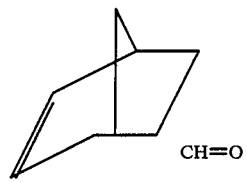
(V)

is either (a) subjected to autocondensation with formation of a compound of the formula VII

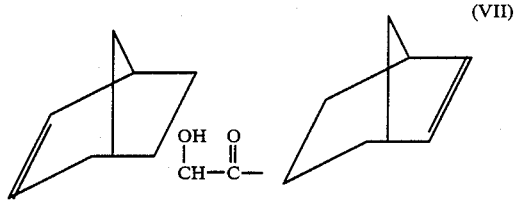
(VII)

or (b) reacted with a compound of the general formula II

R—CH=O (II)

where R has the above meanings, with formation of a mixture of the compounds of the general formulae VIII (a) and (b)

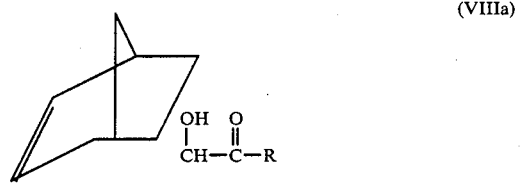

(VIIIa)

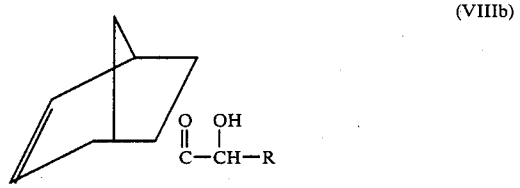

(VIIIb)

where R is as defined above, in the presence of a catalyst, and the compound of the formula VII or the compounds of the formulae VIII (a) and (b) is or are oxidized to the corresponding dicarbonyl compounds, after which gas-phase pyrolysis is carried out at from 500° to 700° C. and under reduced pressure, in particular less than 10⁻¹ mbar, and, if desired, the resulting compound of the general formula I is further purified.

These compounds can be used, for example, as monomer components in polymeric systems.

12 Claims, No Drawings

PREPARATION OF VINYLGLYOXAL DERIVATIVES, NOVEL VINYLGLYOXAL DERIVATIVES AND THEIR USE

The present invention relates to a process for the preparation of vinylglyoxal derivatives, novel vinylglyoxal derivatives and their use as monomer components in polymeric systems.

Methylvinylglyoxal of the formula (I'a)

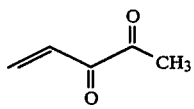

has been postulated as a component of the dione fraction in the tropospheric photooxidation of aromatic hydrocarbons (cf. J. Phys. Chem. 88 (1984), 4122), but the compound as such has not been isolated, nor is it possible to derive a process for its preparation from the literature cited, which furthermore gives no information about the properties of the compound.

Although divinylglyoxal of the formula (I'b)

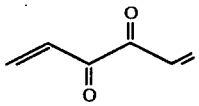

is referred to in terms of its formula in C.R. Acad. Sc. Paris, Series C, pages 233–235 (1971), it is also stated that the compound occurs in traces. The publication describes neither a characterization of this compound nor a procedure which permits the preparation of this compound in an amount which would allow it to be purified and characterized. Since the publication furthermore gives no experimental information about the supposed preparation and any characterization, it must be assumed that this compound is purely speculative and has therefore not been made available to those skilled in the art.

It is an object of the present invention to provide a process for the preparation of vinylglyoxal derivatives of the general formula (I)

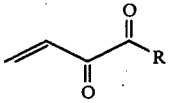

where R is straight-chain or branched alkyl or alkenyl, cycoalkyl or unsubstituted or substituted phenyl.

We have found that this object is achieved by a process wherein bicyclo[2.2.1]hept-5-enecarbaldehyde of the formula V

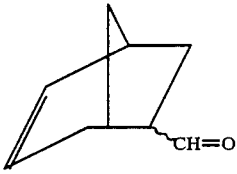

is either (a) subjected to autocondensation with formation of a compound of the formula VII

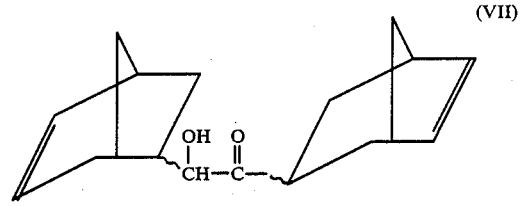

or (b) reacted with a compound of the general formula II

 (II)

where R has the above meanings, with formation of a mixture of the compounds of the general formulae VIII (a) and (b)

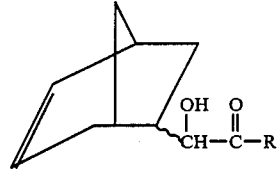

where R is as defined above, in the presence of a catalyst, and the compound of the formula VII or the compounds of the formulae VIII (a) and (b) is or are oxidized to the corresponding dicarbonyl compounds, after which gas-phase pyrolysis is carried out at from 500° to 700° C. and under reduced pressure, in particular less than $10^{-1}$ mbar, and, if desired, the resulting compound of the general formula I is further purified.

In a preferred embodiment of the novel process, the gas-phase pyrolysis is carried out at from 550° to 630° C., in particular from 580° to 600° C., under about $10^{-2}$ mbar.

In a preferred embodiment of the novel process, a compound of the general formula II

 (II)

is used, where R is $C_1$—$C_{20}$-alkyl, in particular $C_1$—$C_4$-alkyl, $C_2$—$C_{20}$-alkenyl, in particular $C_2$—$C_6$-alkenyl, $C_3$—$C_7$-cycloalkyl, or phenyl which is unsubstituted or substituted by halogen, cyano, $C_1$—$C_{12}$-alkyl, in particular $C_1$—$C_4$-alkyl, $C_1$—$C_{12}$-alkoxy, in particular $C_1$—$C_4$-alkoxy, or $CF_3$.

The present invention furthermore relates to compounds of the general formula (I')

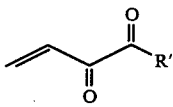

(I')

where R' is $C_1$—$C_{20}$-alkyl, $C_2$—$C_{20}$-alkenyl, $C_3$—$C_7$-cyclo-alkyl, or phenyl which is unsubstituted or substituted by $C_1$—$C_{12}$-alkyl, $C_1$—$C_{12}$-alkoxy, halogen, cyano or $CF_3$.

Particularly preferred compounds of the general formula I' are those in which R' is methyl or vinyl (compounds of the formulae I'a and I'b).

The present invention also relates to the use of the compound of the general formula I or of the general formula I', including the compounds of the formulae I'a and I'b, as monomer components in polymeric systems.

The compounds of the general formula I or I' are, however, also suitable for other applications; for example, the compounds are useful components for chemical syntheses, for example for compounds having pharmacological or pesticidal activity.

Examples of R in the general formula I or R' in the general formula I' are methyl, ethyl, n-propyl, isopropyl, n-butyl, sec-butyl, isobutyl, pentyl, hexyl, heptyl, octyl, vinyl, allyl, butenyl, pentenyl, hexenyl, cyclopropyl, cyclobutyL, cyclopentyl, cyclohexyl, cycloheptyl and phenyl. As defined above, phenyl may be mono-, di- or polysubstituted.

Very generally, the acyloins and 1,2-diketones used in the novel process can also be obtained by other procedures. For example, the reaction of norbornene-carbaldehydes which may also be substituted, with an aldehyde of the general formula II, R—CH=O, also by extrapolation of the measures in Synthesis 1977, 403, is of importance, and the resulting asymmetric acyloins can be separated from the simultaneously formed symmetric acyloins by distillation in the case of compounds in which R is $CH_3$ to $C_4H_9$, and thermolytically in the case of higher homologs and derivatives. However, there are steric limits here. If in fact 3-methylnorborn-5-ene-2-carbaldehyde is reacted with propionaldehyde using a 1,3-thiazolium salt as a catalyst, asymmetric acyloin is obtained in a yield of only 29% of theory. If the aldehyde is subjected to autocondensation, this procedure gives no acyloin at all. The methyl group on carbon atom 3 effectively prevents any nucleophilic addition of the catalyst at the C=O group of the aldehyde (cf. Synthesis 1980, 1, 309).

Another process is described in Chem. Ber. 112 (1978), 2062, and ibid. 114 (1981), 959. The procedure proposed in Synthesis 1969, 17, is also suitable, although, in this procedure, the hydrolysis of the thioketal formed as an intermediate is not without problems (cf. also Synthesis 1977, 357).

In summary, it may be stated that, with a knowledge of conventional procedures, the skilled worker can prepare the acyloins and 1,2-diketones, so that all vinylglyoxal derivatives of the general formulae I and I' can be prepared using the pyrolysis stage of the novel process, in conjunction with either the other measures of the process claims or the above measures of the stated prior art.

The process according to the invention is described below, in particular with reference to the preferred compounds of the formulae I'a and I'b.

Compounds I'a and I'b are prepared by the novel process by gas-phase pyrolysis of the diketones III or IV at 500°–700° C., preferably 600° C., and under reduced pressure, in particular $<10^{-1}$, preferably bout $10^{-2}$, mbar.

Reaction scheme:

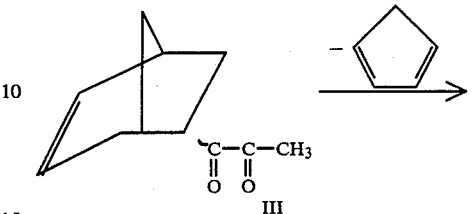

The pure exo or endo isomers or, advantageously, the exo/endo mixtures usually obtained in the preparation of III or IV can be used as educts III and IV.

The pyrolysis in the novel process is particularly advantageously carried out as a flash pyrolysis, since this procedure gives good yields of even thermally unstable products.

The diketones of the general formulae I and I' and the cyclopentadiene formed during the pyrolysis are collected in cold traps; the diketones I and I' can be used without further purification.

The diketones III and IV used as educts are known or can be synthesised by conventional methods. According to Alder and Stein [Liebigs Ann. Chem. 525 (1936), 17], bicyclo[2.2.1]hept-5-ene-1-carbaldehyde is obtained in the form of a mixture of the endo/exo isomers (ratio about 3:1) from acrolein and cyclopentadiene.

The isomer mixture can be separated in principle, although this is not necessary for the pyrolysis step III→I'a or IV→I'b. V is then reacted with V or acetaldehyde (VI) to give the acyloins VII or VIIIa, b by the method proposed by Stetter et al. (Syntheses 1976, 733: 1977, 1403; 1980, 1,309).

Reaction scheme:

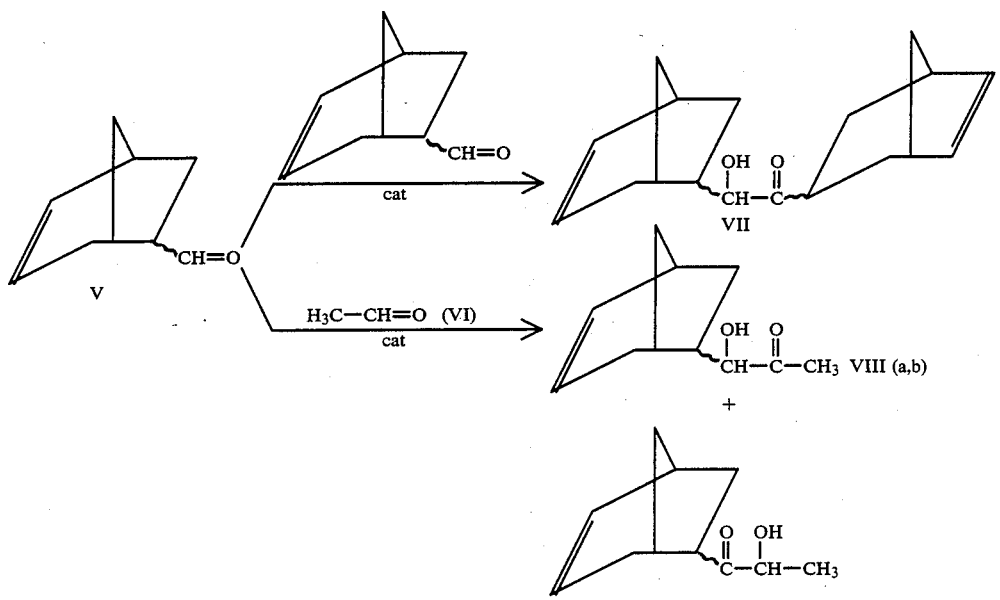

Suitable catalysts are those usually employed for acyloin condensations, as disclosed in, for example, Houben-Weyl, Methoden de organischen Chemie, 4th Edition, Volume 7/2c, page 2207, which are herewith incorporated by reference. 3-Benzyl-5-(2-hydroxyethyl)-4-methyl-1,3-thiazolium chloride [Chem. Ber. 109 (1976), 2890 and Synthesis 1975, 379] is preferably used.

The acyloins VII and VIIIa, b can be oxidized to the diketones III (a, b) or IV by a conventional method (Houben-Weyl, Methoden der organischen Chemie, 4th Edition, Volume 7/2c, page 2233, which is herewith incorporated by reference). Advantageously, $Bi_2O_3$ in glacial acetic acid is used as the oxidizing agent (J. chem. Soc. 1950, 2744, and 1951, 793). The elemental bismuth formed in the reaction from $Bi_2O_3$ can readily be separated from the reaction mixture by filtration and converted again to $Bi_2O_3$, for example by heating in the air.

The Examples which follow illustrate the invention.

EXAMPLE 1

(a) Preparation of endo- and exo-bicyclo[2.2.1]hept-5-ene-2-carbaldehyde (V)

60.0 g (1.10 moles) of freshly distilled acrolein are added dropwise to a solution of 66.0 g (1.00 mole) of freshly cleaved cyclopentadiene in 50 ml of absolute diethyl ether in the course of 10 minutes. During the dropwise addition, the mixture is cooled with ice water. After some time, gentle boiling of the ether is detectable, but soon ceases. The means of cooling is then removed and the mixture is refluxed for a further half hour. 200 ml of ether are added to the cooled reaction mixture, which is then washed several times with water and dried. The solvent is stripped off and the residue is subjected to fractional distillation.

Bp.: 61°–65° C./15.

Yield: 107 g (0.88 mole, 88%).

(b) Preparation of the catalyst 3-benzyl-5-(2-hydroxyethyl)-4-methyl-1,3-thiazolium chloride (X)

71.6 g (500 millimoles) of 5-(2-hydroxyethyl)-4-methyl-1,3-thiazole), 63.3 g (500 millimoles) of freshly distilled benzyl chloride and 250 ml of absolute acetonitrile are refluxed for 24 hours in a 500 ml round-bottomed flask. The stirred reaction mixture is slowly cooled to room temperature, and the precipitate is filtered off under suction, washed colorless with dry acetonitrile, predried and then dried at 90° C. under reduced pressure from a water pump.

mp.: 139°–140° C.

Yield: 108.8 g (400 millimoles, 80%).

(c) Preparation of 1,2-bis-[bicyclo[2.2.1]hept-5-en-2-yl]-ethan-1-on-2-ol (VII)

100.0 g (818 millimoles) of V, 6.7 g (25 millimoles) of X, 150 ml of absolute ethanol and finally 15.2 g (150 millimoles) of dry triethylamine are introduced into a 250 ml three-necked flask equipped with a stirrer, a reflux condenser (with dried tube) and a gas inlet tube for dry nitrogen, and are heated for 12 hours in a gentle stream of nitrogen. The reaction is monitored by gas chromatography (column material: OV 17 on Chromosorb ® WAW 80/100, 48 cm; 10% UCC W 982 on Chromosorb WAW DMCS, 48 cm). After cooling, the reaction mixture is poured onto half a liter of ice/water and extracted with 300 ml of chloroform. The organic phase is washed with dilute sulfuric acid, water and sodium bicarbonate solution and dried. Chloroform is then stripped off and the residue is subjected to fractional distillation.

Bp.: 128°–131° C./0.01.

Mp.: 52°–55° C.

Yield: 65.1 g (266 millimoles, 65%).

(d) Preparation of 1-[bicyclo[2.2.1]hept-5-en-2-yl]-propan-1-ol-2-one (VIII)

12.2 g (100 millimoles) of V, 40 ml (about 0.7 mole) of acetaldehyde, 2.70 g (10.0 millimoles) of catalyst x, and 15 ml of absolute triethylamine are heated for 5 hours in an autoclave (100 ml) equipped with a magnetic stirrer, by means of a hot oil bath (90° C.). After cooling, the reaction mixture is poured onto 200 ml of ice/water. Ten autoclave charges (a larger apparatus was not available) are collected, and extracted with 500 ml of chloroform. The organic phase is washed with dilute sulfuric acid, water and sodium bicarbonate solution and dried over magnesium sulfate. The chloroform is stripped off and the residue is subjected to fractional distillation.

Bp.: 47°–49° C./0.01.

Yield: 74.8 g (450 millimoles, 45% based on V).

(e) Preparation of 1,2-bis-[bicyclo[2.2.1]hept-5-en-2-yl]-ethane-1,2-dione (IV)

49.9 g (204 millimoles) of VII in 130 ml of 2-ethoxyethanol and 40 ml of glacial acetic acid are heated to 105° C., while stirring. 25.0 g (53.6 millimoles) of $Bi_2O_3$ are then added all at once. After a reaction time of 2 hours, the elemental bismuth is filtered off and washed with 300 ml of chloroform. The organic phase is washed neutral with water. The solvent is stripped off and the residue subjected to fractional distillation. The product is then recrystallized from petroleum ether.

Bp.: 98°–100° C./0.01.

Mp.: 47°–49° C.

Yield: 32.0 g (132 millimoles, 66%).

The preparation of III (endo- and exo-[bicyclo[2.2.1]hept-5-en-2-ylpropane-1,2-dione]) is carried out similarly.

Bp.: 94°–95° C./20.

Yield: 21.0 g (128 millimoles, 64%).

Elemental analysis: $C_{10}H_{12}O_2$ (164.20). Calculated: C 73.14 H 7.37. Found: C 73.00 H 7.37. C 73.16 H 7.41.

(f) Preparation of methylvinylglyoxal (I'a)

In a gas-phase pyrolysis apparatus consisting of a small tubular furnace with a quartz tube and a connected vacuum line with four cold traps, the pyrolysis is carried out at 600° C. and under from 0.01 to 0.02 mmHg. The cold traps which are directly adjacent to the furnace and in which the products formed collect are cooled to −78° C. (cold trap 1) and −178° C. (cold trap 2). To carry out the pyrolysis, the stock vessel is heated to 60° C. After about 2 hours, the educt VIII has vanished from the stock vessel, the dione I'a is present in the first cold trap, and the cyclopentadiene formed simultaneously is present in the second cold trap. If four product cold traps are used instead of two, the first, counted from the furnace, is cooled to −78° C. and the fourth to −178° C. The two middle traps initially remain uncooled. Thus, cyclopentadiene passes through them without condensing. This makes it possible to purify the dione by recondensation. The yield of I'a is 89%.

$^1H$—NMR (80 MHz, $CDCl_3$): 6.0–7.3 (ABC—m; 3H, Vinyl-H), 2.47 (s; 3H, $CH_3$).

$^{13}C$—NMR ($CDCl_3$): 24.2 (q; $CH_3$), 128.7 (d; C—4), 133.1 (t; C—5), 186.8 (s; C—3), 197.9 (s; C—2).

IR (Film): 1715 (C=O), 1690 (C=O) $cm^{-1}$.

UV (Ethanol): $\lambda_{max}$=434 nm, $\epsilon$=18.

EXAMPLE 2

Divinylglyoxal (I'b)

The procedure described in Example 1, stage (f) is followed, except that the stock vessel is heated to 110° C. The yield of I'b is 81%.

$^1H$—NMR (80 MHz, $CDCl_3$): 6.0–7.2 (ABC—m; 6H, Vinyl-H).

$^{13}C$—NMR ($CDCl_3$): 130.1 (d; C—2, C—5), 133.0 (t; C—1, C—6), 189.0 (s; C—3, C—4).

IR (Film): 1690 $cm^{-1}$ (C=O).

UV (Ethanol): $\lambda_{max}$=432, $\epsilon$=17.

2: $^1$: H—NMR (80 MHz, $CDCl_3$): 6.0–7.3 (ABC—m; 3H, Vinyl-H), 2.47 (s; 3H, $CH_3$).

$^{13}C$—NMR ($CDCl_3$): 24.2 g (q; $CH_3$:), 128.7 (d; C—4), 133.1 (t; C—5), 186.8 (s; C—3), 197.9 (s; C—2).

IR (Film): 1715 (C=O), 1690 (C=O) $cm^{-1}$.

UV (Ethanol): $\lambda_{max}$=434 nm, $\epsilon$=18.

I'b is hydrogenated by means of Pd/C to the 3,4-hexadione, which is compared with authentic material and found to be identical to it.

EXAMPLES 3 TO 6

The procedure described in Example 1 (stages d to f) is followed, except that in stage d the following aldehydes of the formula II are used instead of acetaldehyde:

Examples (3) R=$C_2H_5$ (4) R=n—$C_3H_7$ (5) R=i—$C_3H_7$ (6) R=$C_6H_5$

The resulting acyloins of the formula VIII are oxidized with $Bi_2O_3$, similarly to Example 1e, to the corresponding diketones, which are subjected to gas-phase thermolysis (600° C./0.01 mmHg) as described in Example 1f to give the vinylglyoxals of the formula I (yield of the pyrolysis stage given in parentheses in % of theory):

EXAMPLE 3 R=$C_2H_5$ (80%)

1-hexene-3,4-dione $^1H$—NMR (300 MHz, $CDCl_3$/TMS): δ (ppm)=6.52 (dd, 1H, J=18 Hz, $^2J$=1.5 Hz); 6.05 (dd, 1H, J=11 Hz, $^2J$=1.5 Hz); 7.01 (dd, 1H, J=18 Hz, J=11 Hz); 2.84 (q, 2H, J=7 Hz); 1.12 (t, 3H, J=7 Hz).

$^{13}C$—NMR (75 MHz, $CDCl_3$/TMS): δ (ppm)=133.5 (C—1); 129.3 (C—2); 187.9 (C—3); 201.2 (C—4); 30.2 (C—5); 6.9 (C—6).

IR spectrum (Film, $cm^{-1}$): 2990, 2960, 2890, 1690, 1610, 1455, 1080, 980, 905.

MS (70 eV, m/e): 112 ($M^+$, 10%); 57 (100%); 55 (73%).

UV (cyclohexane): $\lambda_{max}$=440 nm ($\epsilon$=21); 238 nm ($\epsilon$=5500).

EXAMPLE 4 R=n—$C_3H_7$ (80%)

1-heptene-3,4-dione $^1H$—NMR (300 MHz, $CDCl_3$/TMS): δ (ppm)=6.51 (dd, 1H, J=17 Hz, $^2J$=1.5 Hz); 6.05 (dd, 1H, J=11 Hz, $^2J$=1.5 Hz); 7.00 (dd, 1H, J=17 Hz; J=11 Hz); 2.79 (t, 2H, J=7 Hz); 1.65 (tq, 2H, J=7 Hz, J=7 Hz); 0.96 (t, 3H, J=7 Hz).

$^{13}$C—NMR (75 MHz, CDCl$_3$/TMS): δ (ppm)=133.4 (C—1); 129.3 (C—2); 187.9 (C—3); 200.7 (C—4); 38.6 (C—5); 16.6, 13.7 (C—6 or C—7).

IR spectrum (Film, cm$^{-1}$): 2970, 2940, 1710, 1690, 1605, 1450, 1400, 1100, 950.

MS (70 eV, m/e): 125 (M$^+$, 6%); 61 (67%); 55 (86%); 43 (100%).

UV Cyclohexane): λ$_{max}$=444 nm (ε=21); 238 nm (ε=5000).

EXAMPLE 5 R=iso—C$_3$H$_7$ (80%)

5-Methyl-1-hexen-3,4-dione $^1$H—NMR (300 MHz, CDCl$_3$/TMS): δ (ppm)=6.47 (dd, 1H, J=17 Hz, $^2$J=1.5 Hz); 6.07 (dd, 1H, J=11 Hz, $^2$J=1.5 Hz); 6.93 (dd, 1H, J=17 Hz, J=11 Hz); 3.39 (sept., 1H, J=7 Hz); 1.13 (d, 6H, J=7 Hz).

$^{13}$C—NMR (75 MHz, CDCl$_3$/TMS): δ (ppm)=133.5 (C—1); 130.3 (C—2); 189.3 (C—3); 204.2 (C—4); 34.6 (C—5); 17.2 (C—6, C—7).

IR spectrum (Film, cm$^{-1}$): 2980, 2940, 2880, 1700, 1605, 1460, 1400, 975, 930, 845.

UV (Cyclohexane): λ$_{max}$=449 nm (ε22); 238 nm (ε=400).

MS (70 eV, m/e): 126 (M$^+$, 5%); 61 (41%); 55 (64%); 43 (100%).

EXAMPLE 6 R=C$_6$H$_5$ (75%)

1-Phenyl-3-buten-1,2-dione $^1$H—NMR (300 MHz, CDCl$_3$/TMS): δ (ppm)=6.41 (dd, 1H, J=18 Hz, $^2$J=0.6 Hz); 6.24 (dd, 1H, J=11 Hz, $^2$J=0.6 Hz); j6.75 (dd, 1H, J=18 Hz, J=11 Hz); 7.95–7.99 (m, 2H$_{ortho}$); 7.47–7.54 (m, 2H$_{meta}$); 7.62–7.68 (m, 1H$_{para}$).

$^{13}$C—NMr (75 MHz, CDCl$_3$/TMS): δ (ppm)=134.8 (C—4); 132.7 (C—3); 192.9, 193.3 (C—1, C—2); 132.5 (C$_i$); 130.0 (2C$_{ortho}$); 128.9 (2C$_{meta}$); 134.8 (C$_{para}$).

We claim:

1. A compound of the formula

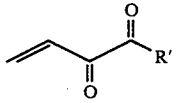 (I')

where R' is methyl, ethyl, n-propyl, iso-propyl, n-butyl, iso-butyl, hexyl, heptyl, octyl, allyl, butenyl, pentenyl, hexenyl, C$_3$—C$_7$-cycloalkyl, or phenyl which is unsubstituted or substituted by C$_1$—C$_{12}$-alkyl, C$_1$—C$_{12}$-alkoxy, halogen, cyano or CF$_3$.

2. A compound of the formula I' as claimed in claim 1, wherein R' is methyl, ethyl, n-propyl, iso-propyl, n-butyl, iso-butyl, allyl, butenyl, pentenyl, hexenyl, C$_3$—C$_7$-cycloalkyl, or phenyl which is unsubstituted or substituted by C$_1$—C$_4$-alkyl, C$_1$—C$_4$-alkoxy, halogen, cyano or CF$_3$.

3. A compound of the formula I' as claimed in claim 1, where R' is methyl or allyl.

4. A compound of the formula I' as claimed in claim 1, wherein R' is methyl, ethyl, n-propyl, iso-propyl, n-butyl, iso-butyl, allyl, cyclopropyl or phenyl which is unsubstituted or substituted by C$_1$—C$_4$-alkyl, C$_1$—C$_4$-alkoxy, halogen, cyano or CF$_3$.

5. The compound of the formula I' as claimed in claim 1, which is allylvinylglyoxal.

6. The compound of the formula I' as claimed in claim 1, which is methylvinylglyoxal.

7. The compound of the formula I' as claimed in claim 1, which is 1-hexene-3,4-dione.

8. The compound of the formula I' as claimed in claim 1, which is 1-heptene-3,4-dione.

9. The compound of th formula I' as claimed in claim 1, which is 5-methyl-1-hexene-3,4-dione.

10. The compound of the formula I' as claimed in claim 1, which is 1-phenyl-3-buten-1,2-dione.

11. A compound of the formula:

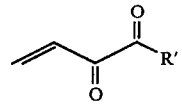

where R' is allyl, butenyl, pentenyl or hexenyl.

12. A compound of the formula

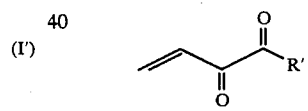

where R' is C$_3$—C$_7$-cycloalkyl or phenyl which is unsubstituted or substituted by C$_1$—C$_{12}$-alkyl, C$_1$—C$_{12}$-alkoxy, halogen, cyano or CF$_3$.

* * * * *